(12) United States Patent
Sobek et al.

(10) Patent No.: US 9,227,189 B2
(45) Date of Patent: Jan. 5, 2016

(54) MICROFLUIDIC LIQUID STREAM CONFIGURATION SYSTEM

(75) Inventors: Daniel Sobek, Portola Valley, CA (US); Jun Zeng, Burlington, MA (US)

(73) Assignee: Zymera, Inc., San Jose, CA (US)

( * ) Notice: Subject to any disclaimer, the term of this patent is extended or adjusted under 35 U.S.C. 154(b) by 1941 days.

(21) Appl. No.: 12/064,630

(22) PCT Filed: Aug. 23, 2006

(86) PCT No.: PCT/US2006/033068
§ 371 (c)(1),
(2), (4) Date: Feb. 23, 2008

(87) PCT Pub. No.: WO2007/025041
PCT Pub. Date: Mar. 1, 2007

(65) Prior Publication Data
US 2008/0251383 A1    Oct. 16, 2008

Related U.S. Application Data

(60) Provisional application No. 60/596,015, filed on Aug. 23, 2005.

(51) Int. Cl.
*G01N 27/00* (2006.01)
*B01L 3/00* (2006.01)
*F04B 19/00* (2006.01)
*G01N 33/49* (2006.01)

(52) U.S. Cl.
CPC ..... *B01L 3/502792* (2013.01); *B01L 3/502738* (2013.01); *F04B 19/006* (2013.01); *G01N 33/4905* (2013.01); *B01L 3/50273* (2013.01); *B01L 2300/069* (2013.01); *B01L 2300/0645* (2013.01); *B01L 2300/089* (2013.01); *B01L 2400/0415* (2013.01); *B01L 2400/0448* (2013.01); *B01L 2400/06* (2013.01)

(58) Field of Classification Search
CPC ............ B01I 2400/06; B01I 2400/0415; B01I 3/502738; B01I 3/502792; B01I 2300/0645; F04B 19/006; G01N 33/4905
USPC ................. 204/600, 660, 547, 643, 666, 663; 422/68.1, 99, 100; 137/803–842; 137/601.01–602
See application file for complete search history.

(56) References Cited

U.S. PATENT DOCUMENTS 4,390,403 A    6/1983    Batchelder
5,064,541 A    11/1991   Jeng et al.
(Continued)

OTHER PUBLICATIONS

Srinivasan et al., "An integrated digital microfluidic lab-on-a-chip for clinical diagnostics on human physiological fluids", Royal Society of Chemistry 2004, Lab Chip, May 26, 2004, vol. 4, pp. 310-315.

*Primary Examiner* — Gurpreet Kaur
(74) *Attorney, Agent, or Firm* — Ishimaru & Associates LLP

(57) ABSTRACT

A microfluidic liquid stream configuration system is provided including providing a substrate; forming a first co-planar electrode and a second co-planar electrode on the substrate; applying a dielectric layer, with a controlled surface energy, on the first co-planar electrode and the second co-planar electrode; forming an input reservoir on the first co-planar electrode and a second co-planar electrode; supplying a liquid in the input reservoir for analysis; and imposing an electric field, an electric field gradient, or a combination thereof on the liquid for respectively driving surface charge or dipole moments in the liquid for configuring a liquid stream.

19 Claims, 13 Drawing Sheets

(56) References Cited

U.S. PATENT DOCUMENTS

| | | |
|---|---|---|
| 6,555,389 B1 * | 4/2003 | Ullman et al. ................ 436/514 |
| 6,866,762 B2 | 3/2005 | Gascoyne et al. |
| 6,911,132 B2 * | 6/2005 | Pamula et al. ................ 204/600 |
| 7,267,752 B2 * | 9/2007 | King et al. .................... 204/547 |
| 2002/0182627 A1 | 12/2002 | Wang et al. |
| 2002/0195345 A1 * | 12/2002 | Bentsen et al. ............... 204/600 |
| 2006/0226012 A1 * | 10/2006 | Kanagasabapathi et al. . 204/547 |

\* cited by examiner

MICROFLUIDIC LIQUID STREAM CONFIGURATION SYSTEM

CROSS-REFERENCE TO RELATED APPLICATION

This application claims the benefit of U.S. Provisional Patent Application Ser. No. 60/596,015 filed 23 Aug. 2005.

TECHNICAL FIELD

The present invention relates generally to the electrically controlled movement of small liquid samples, and more particularly to a system of microfluidic system architecture for dynamic routing of a liquid stream.

BACKGROUND ART

There are clinical and analytical chemistry applications that require precise manipulation of small liquid samples. For example, the analysis of a whole blood specimen may require several manipulations including separation of erythrocytes, leukocytes, and platelets from plasma; dispensing the plasma to one or more reaction volumes; mixing reagents; incubating plasma and reagent mixtures; and performing optical or electrochemical measurement of the treated samples. In addition, advanced protocols may require separating different plasma proteins.

Depending on the overall system requirements, the analyte or liquid movement may be driven by a pressure or displacement source, capillary forces, electroosmotic forces, thermocapillary forces, magnetohydrodynamic forces, centrifugal forces, acoustic energy, or electrophoresis. In many of these applications, the pumps, power supplies, valves, motors, and other hardware needed to implement a complete system are much larger and more expensive than the microfluidic component.

Several technologies have been developed in an effort to minimize sample volume and integrate more system functions within a single device. In one, droplets are immersed in a second dielectric (e.g., water droplets surrounded by a working fluid with a lower dielectric constant) employing a plurality of segmented planar electrodes arranged on top and bottom of a liquid housing.

In another, planar electrodes are used to move a drop of fluid from one electrode to the other. Forces of electrical origin cause the droplet movement. In some cases, depending on the properties of the liquid in the droplet and surrounding working fluid, and the characteristics of the electrode arrangement and excitation frequency, the net effect may be an observable change in contact angle at the tri-phase contact line between a solid, the droplet, and the working fluid. This contact angle change is termed "electrowetting."

The use of electrical forces has been demonstrated by non-capillary rising of an essentially non-conductive liquid between two metal plates partially immersed in the fluid, one at ground and the other one at a high voltage. As seen in equation (1), the electrical force density on a piece-wise uniform incompressible linear dielectric liquid, $f^e$, is generated by either the presence of a charge density, $\rho$, driven by an electric field, $\bar{E}$; or by the action of the gradient of the scalar $\bar{E} \cdot \bar{E}$ (i.e., the square of the electric field magnitude) on a polarizable material with a dielectric constant $\in_r$ relative to the permittivity of free space, $\in_0$. The first term in (1) is the Coulombic force density and the second term is the Kelvin polarization force density (also known as the dielectrophoretic force density on the liquid).

$$f^e = \rho \bar{E} + \frac{1}{2}\varepsilon_o(\varepsilon_r - 1)\nabla(\bar{E} \cdot \bar{E}) \qquad (1)$$

For a liquid with spatially uniform properties, the Kelvin polarization force density can only be generated when the geometry of the electrodes establishes an electric field gradient in the liquid. In a conductive liquid with a short dielectric relaxation time compared to the period of the voltage excitation waveform, internal electric fields and electric field gradients are reduced. In the limit of a perfect conductor, the internal field is null. Thus, as the conductivity of the liquid is increased, internal fields are reduced, and charge accumulates at material interface regions. In such cases, Coulombic forces acting on the surface charge at material interfaces are the primary contributors to the electrical force density.

Another technology relies on liquid actuation provided by the Kelvin polarization force (liquid dielectrophoresis). In that case, low to moderate conductivity liquids are handled by modulating the electric field such that the period of the applied voltage oscillations is much smaller than the characteristic relaxation time for the system.

Generally, these technologies require the use of an immiscible working fluid surrounding aqueous droplets (e.g., octyl alcohol and silicon oil, respectively) for best results. Partitioning of chemical constituents from the droplets to the surrounding working fluid is a concern for these two technologies.

In further technologies, co-planar electrode strips covered by a thin dielectric are used as a means for generating a "dielectrophoretic liquid finger" and a string of droplets when the electric field is removed. In these technologies the cross-sectional shape of the finger changed depending on the applied frequency of the field.

Thus, a need still remains for a microfluidic liquid stream configuration system, for biochemical assay analysis, that is capable of dynamically configuring a liquid stream using no moving parts and a minimum of external components. Such system would enable implementing complex biochemical or molecular chemistry analyses in a compact and inexpensive system, making it ideally suitable for point-of-care diagnostics or for home-based diagnostics. Solutions to these problems have been long sought but prior developments have not taught or suggested any solutions and, thus, solutions to these problems have long eluded those skilled in the art.

DISCLOSURE OF THE INVENTION

The present invention provides a microfluidic liquid stream configuration system including providing a substrate; forming a first co-planar electrode and a second co-planar electrode on the substrate; applying a dielectric layer, with a controlled surface energy, on the first co-planar electrode and the second co-planar electrode; forming an input reservoir on the first co-planar electrode and a second co-planar electrode; supplying a liquid in the input reservoir for analysis; and imposing an electric field, an electric field gradient, or a combination thereof on the liquid for respectively driving surface charge or dipole moments in the liquid for configuring a liquid stream.

Certain embodiments of the invention have other aspects in addition to or in place of those mentioned above. The aspects will become apparent to those skilled in the art from a reading of the following detailed description when taken with reference to the accompanying drawings.

BEST MODE FOR CARRYING OUT THE INVENTION

Figure 1:
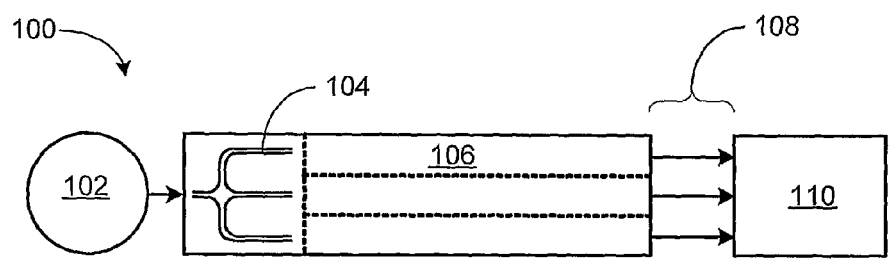
FIG. 1 is a block diagram of a microfluidic liquid stream configuration system, in an embodiment of the present invention.

The following embodiments are described in sufficient detail to enable those skilled in the art to make and use the invention. It is to be understood that other embodiments would be evident based on the present disclosure, and that process or mechanical changes may be made without departing from the scope of the present invention.

In the following description, numerous specific details are given to provide a thorough understanding of the invention. However, it will be apparent that the invention may be practiced without these specific details. In order to avoid obscuring the present invention, some well-known circuits, system configurations, and process steps are not disclosed in detail. Likewise, the drawings showing embodiments of the system are semi-diagrammatic and not to scale and, particularly, some of the dimensions are for the clarity of presentation and are shown greatly exaggerated in the drawing FIGs. Where multiple embodiments are disclosed and described, having some features in common, for clarity and ease of illustration, description, and comprehension thereof, similar and like features one to another will ordinarily be described with like reference numerals.

For expository purposes, the term "horizontal" as used herein is defined as a plane parallel to the plane or surface of the co-planar electrodes, regardless of their orientation. The term "vertical" refers to a direction perpendicular to the horizontal as just defined. Terms, such as "above", "below", "bottom", "top", "side" (as in "sidewall"), "higher", "lower", "upper", "over", and "under", are defined with respect to the horizontal plane. The term "on" means there is direct contact among elements. The term "system" means the method and the apparatus of the present invention. The term "processing" as used herein includes stamping, forging, patterning, exposure, development, etching, cleaning, and/or removal of the material or laser trimming as required in forming a described structure.

Referring now to FIG. 1, therein is shown a block diagram of a microfluidic liquid stream configuration system 100, in an embodiment of the present invention. The block diagram depicts an input reservoir 102, such as an input filter, coagulation monitor, or an input sensor, coupled to a multi-way selection valve 104. The input reservoir 102 is depicted as a circular shape, but it may be another geometric shape such as a rectangle, ellipse, trapezoid, or a triangle. It is for example only that the multi-way selection valve 104 is shown having three outputs and one input. It is understood that the configuration of the multi-way valve 104 may have any number of inputs or outputs. The actuation of the multi-way selection valve 104 is controlled by voltage signals applied to electrical contacts (not shown). The output of the multi-way selection valve 104 provides a liquid stream to an analysis segment 106. The analysis segment 106 may be used to measure the activity of enzymes in a body fluid, or detect the presence of a protein or any other biological or chemical substance in a body fluid. The analysis segment 106 is coupled to stop valves 108, which control the further progression of the liquid to the waste reservoir 110.

The microfluidic liquid stream configuration system 100 may be implemented as an enzyme activity measurement system employing the input reservoir 102, such as an input filter, the multi-way selection valve 104 may also have porous elements (not shown). The analysis segment 106 may contain an enzyme substrate that emits fluorescence in the presence of an enzyme. The first branch of the multi-way selection valve 104 may be the measurement channel; the second branch may be the positive control channel, and the third branch may be the negative control channel. Beyond the analysis segment 106 the stop-valves 108 control the liquid movement to the waste reservoir 110.

Figure 2:
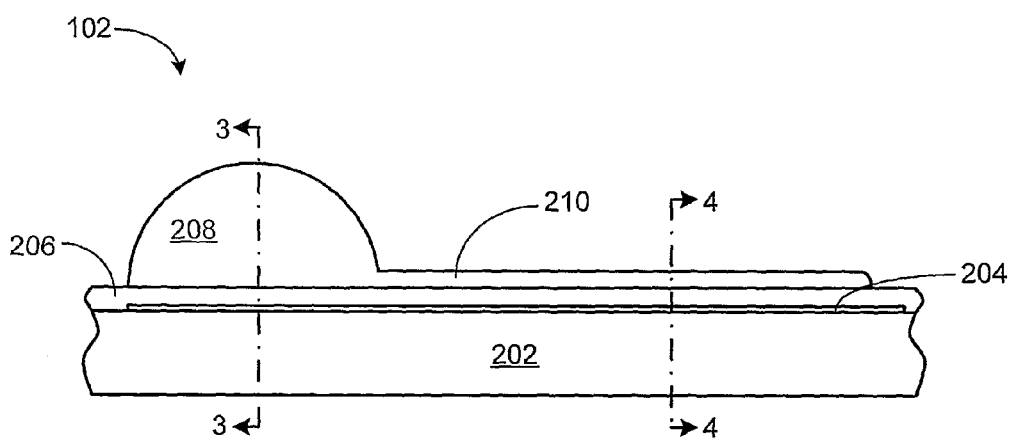
FIG. 2 is a cross-sectional view of the input reservoir, taken along the flow axis.

Referring now to FIG. 2, therein is shown a cross-sectional view of an input reservoir 102 such as a co-planar electrode inlet, taken along the flow axis. The cross-sectional view depicts a substrate 202, such as glass, semiconductor, or plastic substrate. A co-planar electrode 204 is formed on the substrate 202. The co-planar electrode 204 is a metallic strip on the substrate 202. A dielectric layer 206 covers the co-planar electrode 204 and the substrate 202. The co-planar electrode 204 is laid out in parallel pairs along the selected route of a liquid 208 contained in the input reservoir 102 and to be analyzed. When the co-planar electrode 204 is energized, the liquid 208 forms a liquid stream 210 using "electrohydrodynamic actuation".

Electrohydrodynamic actuation is the driving force for moving the liquid 208. It is provided by electric fields and electric field gradients driving surface charge and dipole moments in the liquid 208, respectively.

Figure 3:
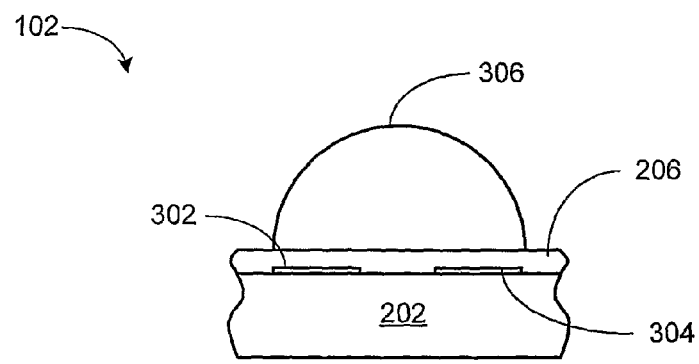
FIG. 3 is a cross-sectional view of input reservoir taken along the section line 3-3 of FIG. 2.

Referring now to FIG. 3, therein is shown a cross-sectional view of the input reservoir 102 such as the co-planar electrode inlet taken along the section line 3-3 of FIG. 2. The substrate 202 supports the first co-planar electrode 302 and the second co-planar electrode 304 positioned parallel to each other along the desired path of the liquid stream 210, of FIG. 2. The first co-planar electrode 302 is coplanar with the second co-planar electrode 304. The dielectric layer 206 encapsulates the first co-planar electrode 302, the second co-planar electrode 304, and the substrate 202. A droplet 306 of the liquid 208, of FIG. 2, is formed on the dielectric layer 206. The surface tension of the droplet 306 maintains the "dome" shape characteristic of the liquid 208.

Figure 4:
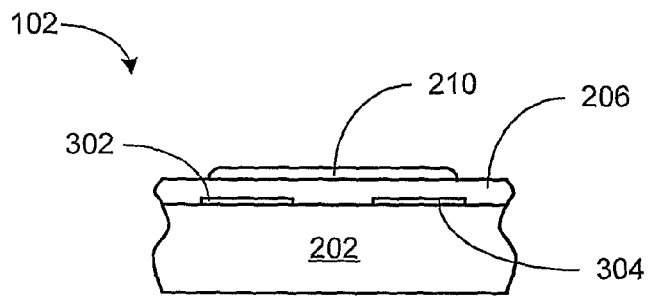
FIG. 4 is a cross-sectional view of a liquid stream, taken along the section line 4-4 of FIG. 2.

Referring now to FIG. 4, therein is shown a cross-sectional view of the input reservoir 102, such as a co-planar electrode inlet, taken along the section line 4-4 of FIG. 2. The substrate 202 supports the first co-planar electrode 302 and the second co-planar electrode 304 positioned parallel to each other along the desired path of the liquid stream 210, of FIG. 2. The dielectric layer 206 encapsulates the first co-planar electrode 302, the second co-planar electrode 304, and the substrate 202. The shape of the liquid stream 210 is caused by the electrohydrodynamic forces induced by the energized first co-planar electrode 302 and the second co-planar electrode 304.

Figure 5:
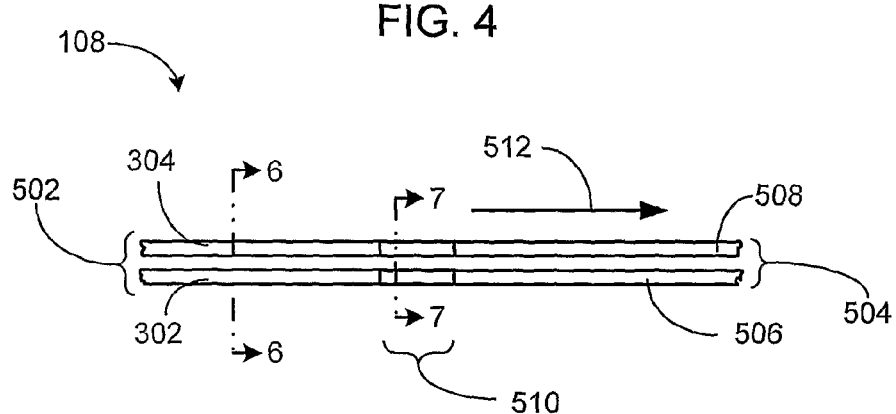
FIG. 5 is a block diagram of a stop valve, in an embodiment of the present invention.

Referring now to FIG. 5, therein is shown a block diagram of the stop valve 108, in an embodiment of the present invention. The block diagram depicts the first co-planar electrode 302 and the second co-planar electrode 304 in a first aligned pair 502. A second aligned pair 504 may be comprised of the third co-planar electrode 506 and the fourth co-planar electrode 508. The second aligned pair 504 is mounted over the first aligned pair 502. An overlap region 510 defines the area where the movement of the liquid stream 210, of FIG. 2, may be halted.

As an example of the operation of the stop valve 108, the liquid stream 210 will move along the first aligned pair 502 when a voltage is applied between the first co-planar electrode 302 and the second co-planar electrode. The voltage may be a DC voltage, an AC voltage, or a combination thereof. The liquid stream 210 may stop flowing when it reaches the end of the first aligned pair 502. Provided no voltage is applied across the second aligned pair 504, this configuration corresponds to the valve in the "closed" position. If a substantially similar voltage is applied across the second aligned pair 504, the valve is "opened" and the liquid stream 210 will again move in the direction of flow 512. With a substantially similar voltage applied across both the first aligned pair 502 and the second aligned pair 504, the liquid stream 210 moves in the direction of flow 512, past the overlap region 510 and continues along the path of the second aligned pair 504.

Figure 6:
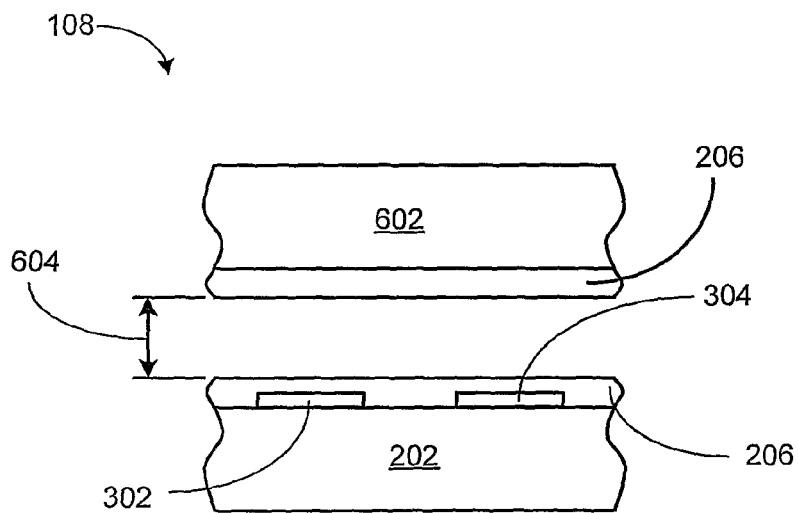
FIG. 6 is a cross-sectional view of the stop valve, taken along the section line 6-6 of FIG. 5.

Referring now to FIG. 6, therein is shown a cross-sectional view of the stop valve 108, taken along the section line 6-6 of FIG. 5. The cross-sectional view depicts the substrate 202 having the first co-planar electrode 302 and the second co-planar electrode 304 mounted thereon. The dielectric layer 206 encapsulates the first co-planar electrode 302, the second co-planar electrode 304 and the top of the substrate 202. A cover plate 602, with the dielectric layer 206 formed on the bottom, is positioned over the substrate 202. A vertical spacing 604 may be in the range of less than 1 micron to 300 microns.

Figure 7:
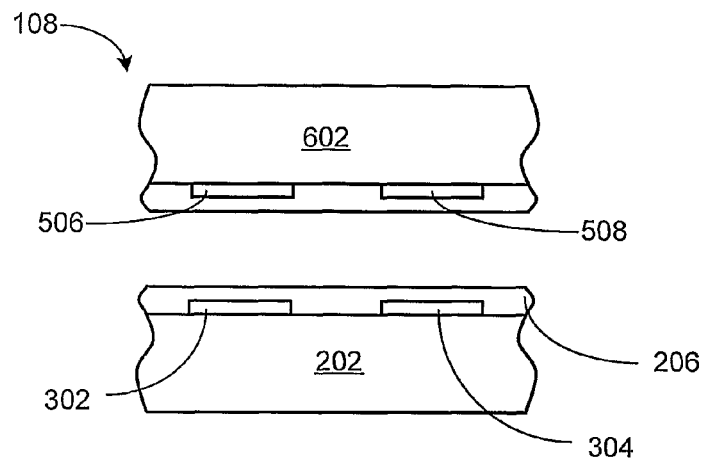
FIG. 7 is a cross-sectional view of the stop valve, taken along the section line 7-7 of FIG. 5.

Referring now to FIG. 7, therein is shown a cross-sectional view of the stop valve 108, taken along the section line 7-7 of FIG. 5. The cross-sectional view depicts the substrate 202 having the first co-planar electrode 302 and the second co-planar electrode 304 mounted thereon. The dielectric layer 206 encapsulates the first co-planar electrode 302, the second co-planar electrode 304, and the top of the substrate 202. The cover plate 602 has the third co-planar electrode 506 and the fourth co-planar electrode 508 formed on the bottom of the cover plate 602. The dielectric layer 206 encapsulates the third co-planar electrode 506, the fourth co-planar electrode 508 and the cover plate 602 bottom. The position of the cover plate 602 is such that the third co-planar electrode 506 vertically overlaps the first co-planar electrode 302 and the fourth co-planar electrode 508 vertically overlaps the second co-planar electrode 304.

Figure 8A:
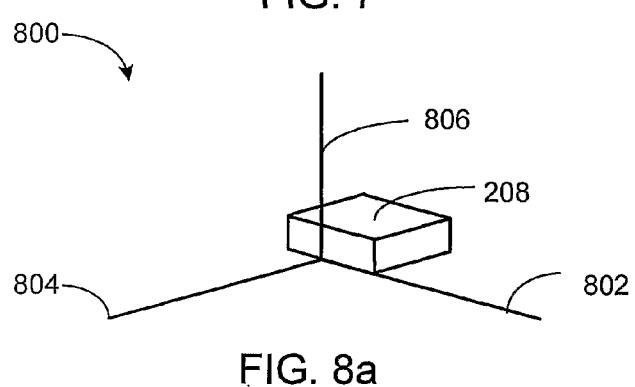
FIG. 8a is a first simulation step of an initial condition for electrohydrodynamic actuation of a liquid held in position by capillary forces.

Referring now to FIG. 8a, therein is shown a first simulation step of an initial condition for electrohydrodynamic actuation of a liquid 208 held in position by capillary forces. The first simulation step depicts a volume of liquid 208 as it would be in a rectangular shaped version of the input reservoir 108, of FIG. 1. The simulation is intended to examine how the liquid 208 reacts with a voltage applied to the co-planar electrode 204 in the input reservoir 102 of FIG. 2. In this figure the volume of the liquid 208 is not moving and is held in position by capillary forces. The volume of liquid 208 is positioned on a set of axis, an X axis 802, a Y axis 804, and a Z axis 806. For the purposes of the simulation the first aligned pair 502 (not shown) extends away from the liquid 208 parallel to the Y axis 804. With no voltage applied to the first aligned pair 502, the liquid 208 remains at rest.

Figure 8B:
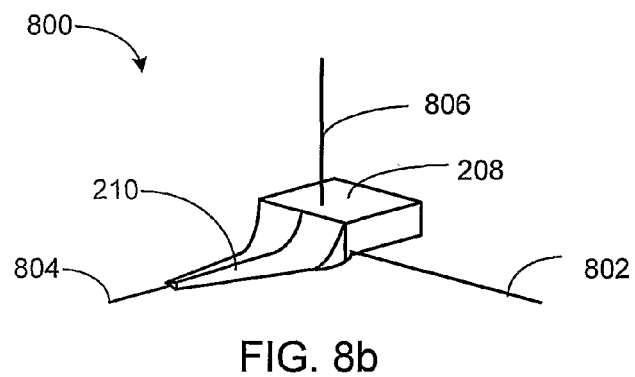
FIG. 8b is a second simulation step of the liquid, 60 microseconds after the application of a voltage across the electrodes.

Referring now to FIG. 8b, therein is shown a second simulation step of the liquid 208, 60 microseconds after the simulation start. The simulation start is analogous to applying a voltage to the first aligned pair 502 (not shown). The resulting electrical field exerts an electro-hydrodynamic force on the liquid 208 and draws it along the Y axis 804. Initially the front of the liquid 208 extends along the Y axis forming the liquid stream 210. The liquid stream 210 continues to extend along the Y axis owing to the electrohydrodynamic force. When the portion of the liquid 208 extruded out of the initial position becomes large, the surface tension will pull the bulk of the liquid along with the liquid stream 210. The footprint of the first aligned pair 502 limits the breadth of the liquid stream 210 in x-y plane because the electric field decays rapidly with respect to the distance away from the first aligned pair 502. Therefore, without physically having channel sidewalls, the liquid stream 210 width is defined by the design of the first aligned pair 502, the physical properties of the liquid, and the applied voltage. In the first 60 microsecond interval, the entire volume of liquid 208 begins moving in the direction of the Y axis 804.

Figure 8C:
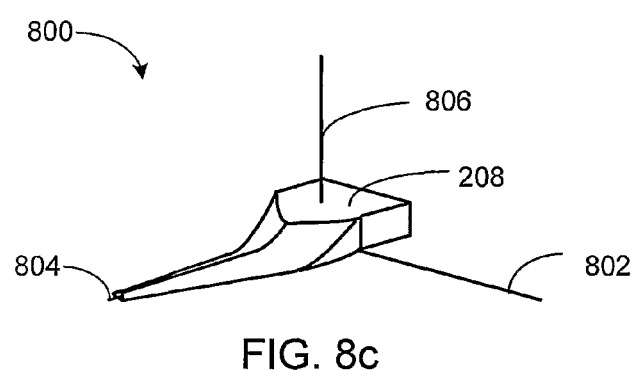
FIG. 8c is a third simulation step of the liquid, 60 microseconds after the second simulation step.

Referring now to FIG. 8c, therein is shown a third simulation step of the liquid 208, 60 microseconds after the second simulation step. The third simulation step depicts the liquid stream 210 continuing along the Y axis 804. The volume of liquid 208 has changed shape as more of the front of the liquid 208 is drawn along the Y axis 804. The liquid stream 210 will continue moving along the Y axis until the end of the first aligned pair 502 is reached.

Figure 9:
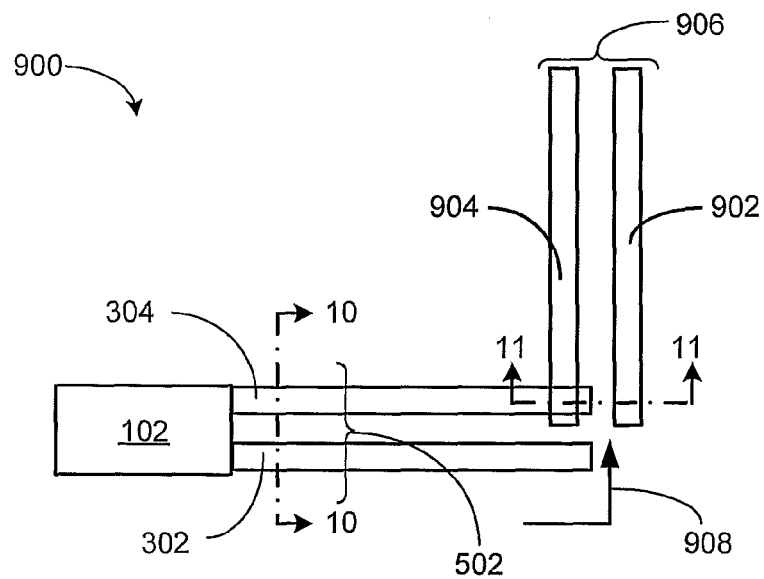
FIG. 9 is a schematic diagram of an L-shaped stop valve, in an embodiment of the present invention.

Referring now to FIG. 9, therein is shown a schematic diagram of an L-shaped stop valve 900, in an embodiment of the present invention. The schematic diagram of the L-shaped stop valve 900 depicts a rectangular version of the input reservoir 102 coupled to the first co-planar electrode 302 and the second co-planar electrode 304. A third co-planar electrode 902 and a fourth co-planar electrode 904 are positioned as a third aligned pair 906 at the end of the second co-planar electrode 304. As described in FIG. 5, the operation of the stop valve 108 is the same as the operation of stop valve 900.

As an example of the operation of the stop valve 900, the liquid stream 210 will move along the first aligned pair 502 when a voltage is applied across the first co-planar electrode 302 and the second co-planar electrode 304. The direction of flow 908 is determined by the direction of the electrodes. The liquid stream 210 may stop flowing when it reaches the end of the first aligned pair 502. Provided no voltage is applied across the third aligned pair 906, this configuration corresponds to the valve in the "closed" position. If a substantially similar voltage is applied across the third aligned pair 906, the valve is "opened" and the liquid stream will again move in the direction of flow 908. With a substantially similar voltage applied across both the first aligned pair 502 and the third aligned pair 906, the liquid stream 210 moves in the direction of flow 908, past the L-shape and continues along the path of the third aligned pair 906.

Figure 10:
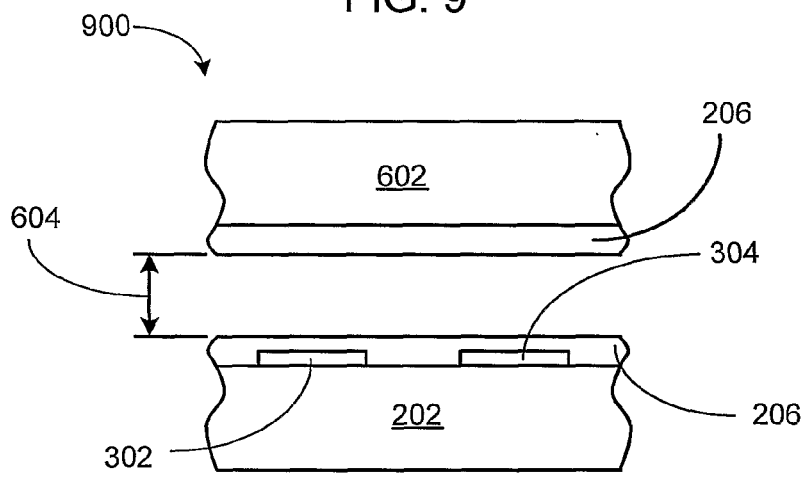
FIG. 10 is a cross-sectional view of the L-shaped-stop valve, taken along the section line 10-10 of FIG. 9.

Referring now to FIG. 10, therein is shown a cross-sectional view of the L-shaped stop valve, taken along the section line 10-10 of FIG. 9. The cross-sectional view depicts the substrate 202 having the first co-planar electrode 302 and the second co-planar electrode 304 mounted thereon. The dielectric layer 206 encapsulates the first co-planar electrode 302, the second co-planar electrode 304 and the top of the substrate 202. The cover plate 602, with the dielectric layer 206 formed on the bottom, is positioned over the substrate 202. A vertical spacing 604 may be in the range of less than 1 micron to 300 microns.

Figure 11:
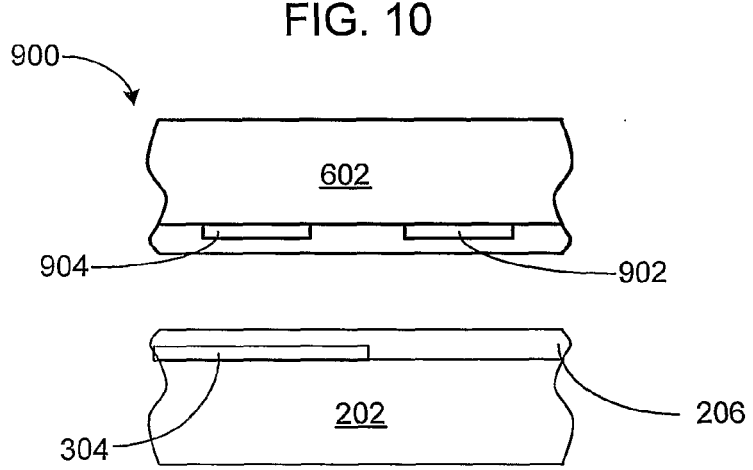
FIG. 11 is a cross-sectional view of the L-shaped stop valve, taken along the section line 11-11 of FIG. 9.

Referring now to FIG. 11, therein is shown a cross-sectional view of the L-shaped stop valve 900, taken along the section line 11-11 of FIG. 9. The cross-sectional view depicts the substrate 202 having the first co-planar electrode 302 and the second co-planar electrode 304 mounted thereon. The dielectric layer 206 encapsulates the first co-planar electrode 302, the second co-planar electrode 304 and the top of the substrate 202. The cover plate 602 has the third co-planar electrode 902 and the fourth co-planar electrode 904 formed on the bottom of the cover plate 602. The dielectric layer 206 encapsulates the third co-planar electrode 902, the fourth co-planar electrode 904 and the cover plate 602 bottom. The position of the cover plate 602 is such that the third co-planar electrode 902 is aligned over the second co-planar electrode 304 forming a 90° angle and the fourth co-planar electrode 904 is aligned parallel to the third co-planar electrode 902.

Figure 12:
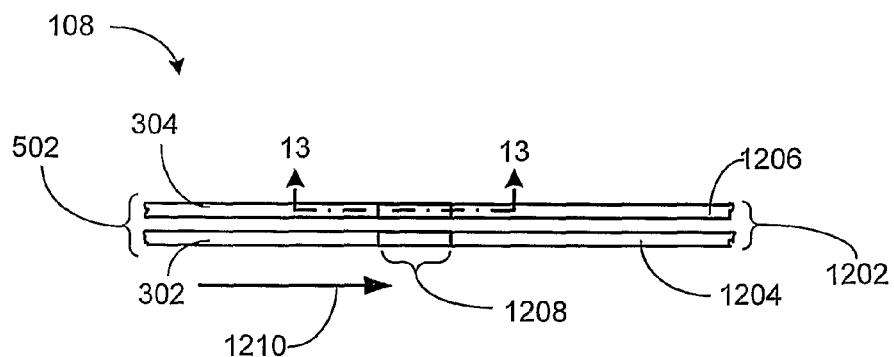
FIG. 12 is a schematic diagram of a stop valve, having overlapping electrodes on a single substrate.

Referring now to FIG. 12, therein is shown a schematic diagram of the stop valve 108, having overlapping electrodes on a single substrate. The schematic diagram depicts the first co-planar electrode 302 and the second co-planar electrode 304 in a first parallel aligned pair 502. A second parallel aligned pair 1202 may be comprised of a first parallel electrode 1204 and a second parallel electrode 1206. The second aligned pair 504 is mounted over the first aligned pair 502. An overlap region 1208 defines the area where the movement of the liquid stream 210, of FIG. 2, may be halted.

As an example of the operation of the stop valve 108, the liquid stream 210 will move along the first aligned pair 502 when a voltage is applied between the first co-planar electrode 302 and the second co-planar electrode. The direction of flow 512 is determined by the electrodes when a voltage is applied. The liquid stream 210 may stop flowing when it reaches the end of the first aligned pair 502. Provided no voltage is applied across the second aligned pair 1202, this configuration corresponds to the valve in the "closed" position. If a substantially similar voltage is applied across the second aligned pair 1202, the valve is "opened" and the liquid stream 210 will again move in the direction of flow 1210. With a substantially similar voltage applied across both the first aligned pair 502 and the second aligned pair 1202, the liquid stream 210 moves in the direction of flow 1210, past the overlap region 1208 and continues along the path of the second aligned pair 1202.

Figure 13:
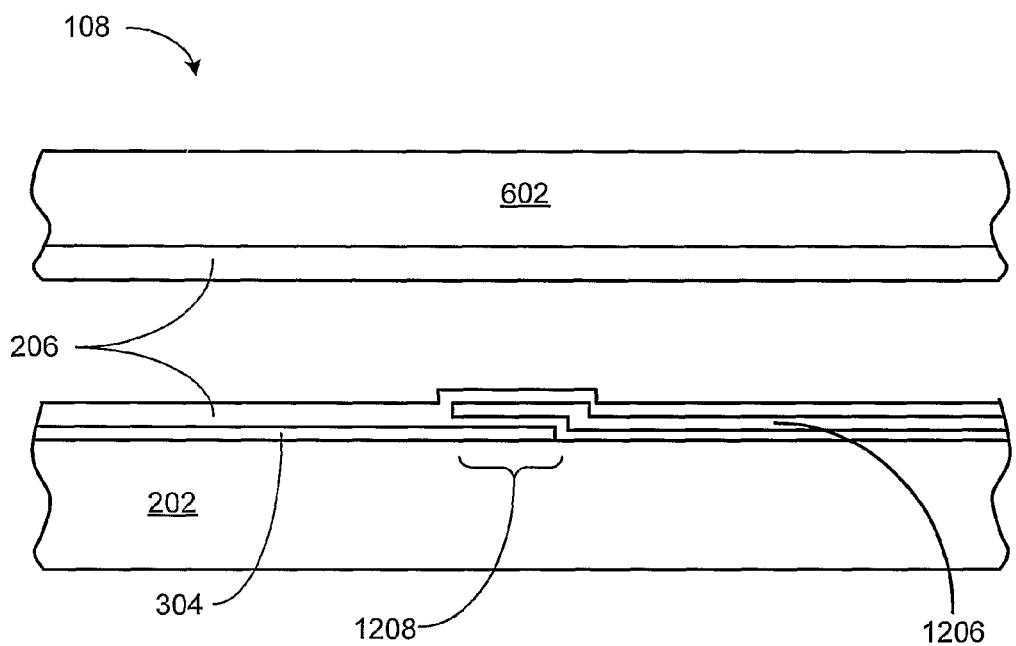
FIG. 13 is a cross-sectional view of the stop valve, taken along the section line 13-13 of FIG. 12.

Referring now to FIG. 13, therein is shown a cross-sectional view of the stop valve, taken along the section line 13-13 of FIG. 12. The cross-sectional view depicts the substrate 202 having the second co-planar electrode 304 mounted thereon. The second parallel electrode 1206 is positioned on the same plane as the second co-planar electrode 304. In the overlap region 1208, the second parallel electrode 1206 is separated from the second co-planar electrode 304 by a thin layer of the dielectric 206. The dielectric layer 206 encapsulates the second co-planar electrode 304, the second parallel electrode 1206 and the top of the substrate 202. The cover plate 602 has an optional thin coating, of the dielectric layer 206, on the bottom.

Figure 14:
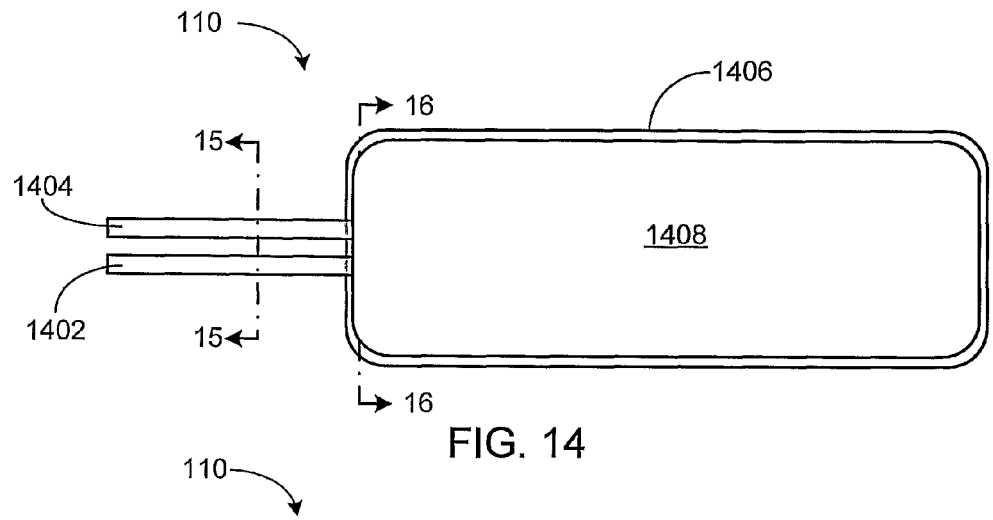
FIG. 14 is a schematic diagram of a waste reservoir, in an embodiment of the present invention.

Referring now to FIG. 14, therein is shown a schematic diagram of a waste reservoir 110, in an embodiment of the present invention. The schematic diagram depicts a first co-planar electrode 1402 and a second co-planar electrode 1404 extending into a waste capture region 1406. The waste capture region 1406 may be implemented using a hydrophilic porous material 1408 patterned in the waste capture region 1406. The hydrophilic porous material 1408 acts as a sink for the liquid 208 and thus enables the continuous electrohydrodynamic actuation of the liquid 208 until the reservoir is full.

Figure 15:
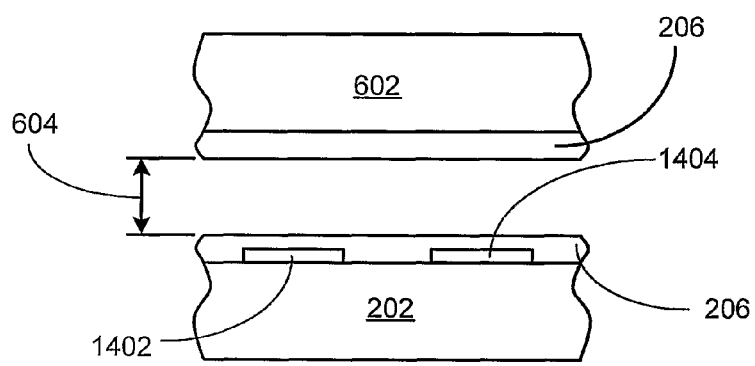
FIG. 15 is a cross-sectional view of the waste reservoir, taken along the section line 15-15 of FIG. 14.

Referring now to FIG. 15, therein is shown a cross-sectional view of the waste reservoir 110, taken along the section line 15-15 of FIG. 14. The cross-sectional view depicts the substrate 202 having the first co-planar electrode 1402 and the second co-planar electrode 1404 mounted thereon. The dielectric layer 206 encapsulates the first co-planar electrode 1402, the second co-planar electrode 1404 and the top of the substrate 202. A cover plate 602, with the optional dielectric layer 206 formed on the bottom, is positioned over the substrate 202. The vertical spacing 604 may be in the range of less than 1 micron to 300 microns.

Figure 16:
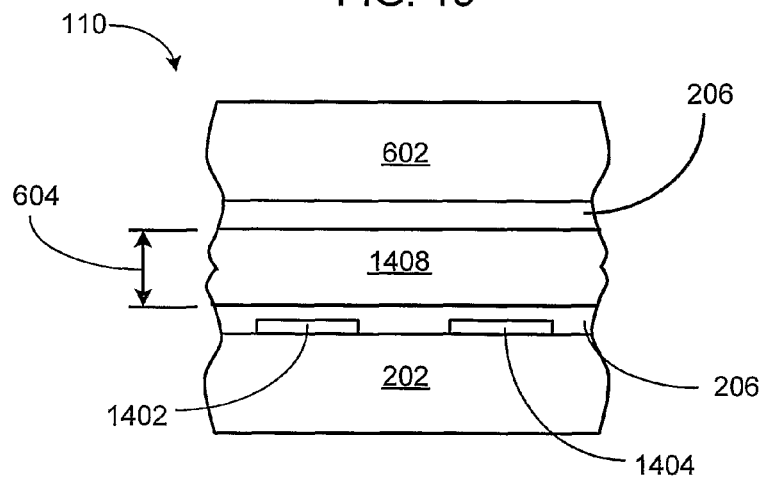
FIG. 16 is a cross-sectional view of the waste reservoir, taken along the section line 16-16 of FIG. 14.

Referring now to FIG. 16, therein is shown a cross-sectional view of the waste reservoir 110, taken along the section line 16-16 of FIG. 14. The cross-sectional view depicts the substrate 202 having the first co-planar electrode 1402 and the second co-planar electrode 1404 mounted thereon. The dielectric layer 206 encapsulates the first co-planar electrode 1402, the second co-planar electrode 1404 and the top of the substrate 202. A cover plate 602, with the dielectric layer 206 formed on the bottom, is positioned over the substrate 202. The vertical spacing 604 is filled with the hydrophilic porous material 1408.

Figure 17:
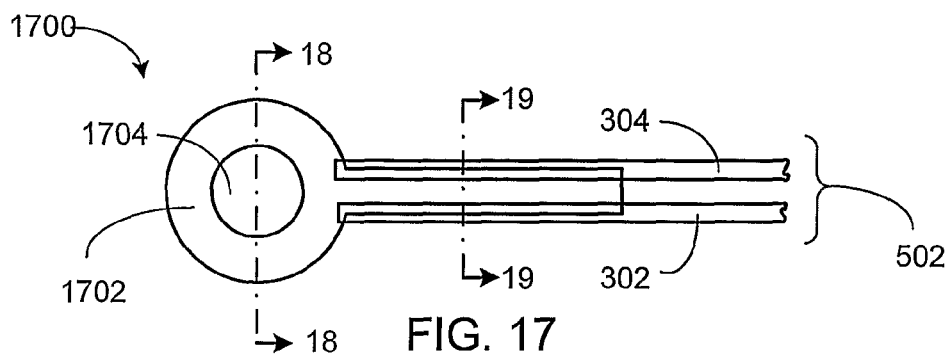
FIG. 17 is a schematic diagram of an electro-hydrodynamic liquid control element, in an embodiment of the present invention.

Referring now to FIG. 17, therein is shown a schematic diagram of an electrohydrodynamic liquid control element 1700, in an embodiment of the present invention. The schematic diagram depicts a porous material 1702 having the input reservoir 1704 over it. The surface energy of the porous material is carefully controlled to both allow wicking of the fluid and electrohydrodynamic actuation out of the porous region. The first co-planar electrode 302 and the second co-planar electrode 304 form the first parallel aligned pair 502, which extends under a section of the porous material 1702 that extends under the input reservoir 1704.

A filter may be implemented by using the porous material 1702 and the first parallel aligned pair 502. The input reservoir 1704 may be an opening in the cover plate 602 and the dielectric layer 206 that provides a receptacle for a specimen (not shown). The liquid 208, of FIG. 2, portion of the specimen permeates the porous material 1702, and particles that are bigger than the pore size remain in the porous material 1702. For example, such filter may be employed to remove erythrocytes, leukocytes, and small particle contamination from a whole blood sample. The first parallel aligned pair 502 partially extends under the porous material 1702 to provide a means for moving the liquid 208, which has gone through the filter, out of this region.

Figure 18:
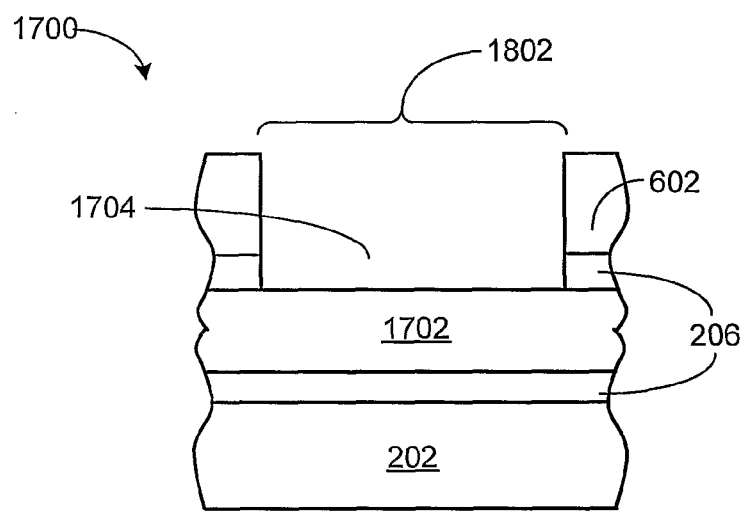
FIG. 18 is a cross-sectional view of the electro-hydrodynamic liquid control element, taken along the section line 18-18 of FIG. 17.

Referring now to FIG. 18, therein is shown a cross-sectional view of the electro-hydrodynamic liquid control element 1700, taken along the section line 18-18 of FIG. 17. The cross-sectional view depicts the substrate 202 having the dielectric layer 206 formed thereon. The porous material 1702 is patterned on the dielectric layer 206 and the cover plate 602, having the dielectric layer 206 on the bottom, may be mounted on the porous material 1702. The input reservoir 1704 may be an opening in the cover plate 602 and the dielectric layer 206 that exposes the porous material 1702 for specimen input.

Figure 19:
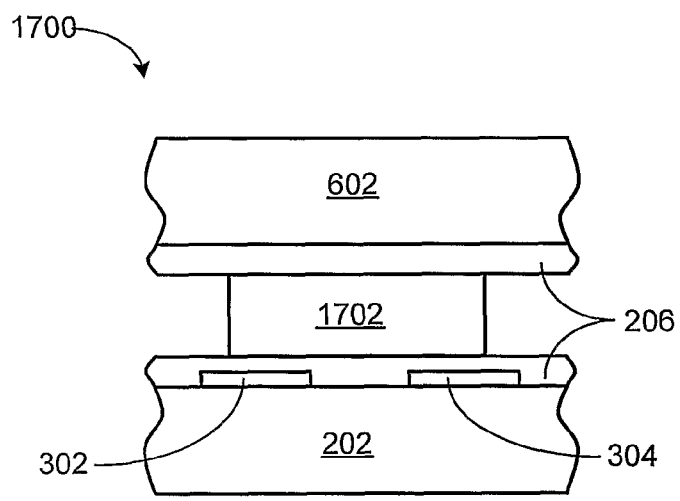
FIG. 19 is a cross-sectional view of the electro-hydrodynamic liquid control element, taken along the section line 19-19 of FIG. 17.

Referring now to FIG. 19, therein is shown a cross-sectional view of the electro-hydrodynamic liquid control element 1700, taken along the section line 19-19 of FIG. 17. The cross-sectional view depicts the substrate 202 having the first co-planar electrode 302 and the second co-planar electrode 304 mounted thereon. The dielectric layer 206 encapsulates the first co-planar electrode 302, the second co-planar electrode 304 and the top of the substrate 202. The porous material 1702 is patterned on the dielectric layer 206 so that the porous material 1702 overlaps the first co-planar electrode 302 and the second co-planar electrode 304. The cover plate 602, with the dielectric layer 206 formed on the bottom, is positioned over the porous material 1702.

Figure 20:
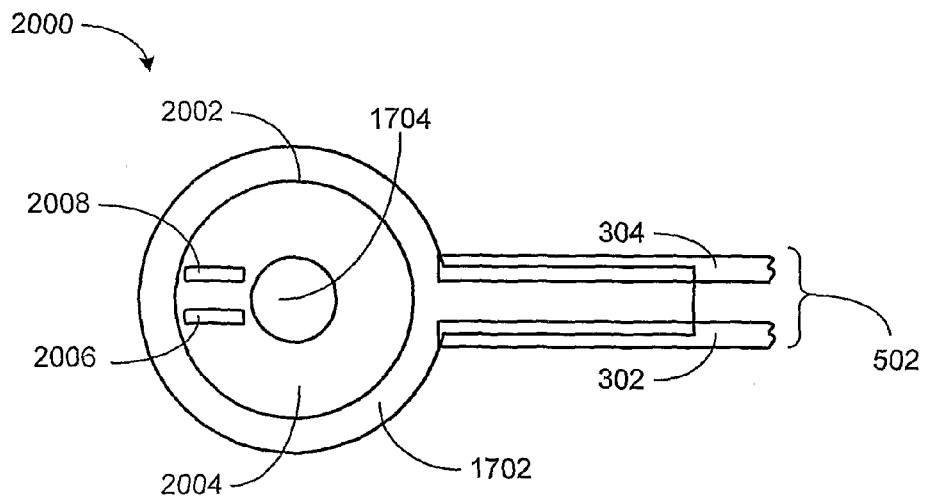
FIG. 20 is a top view of a coagulation measurement device, in an embodiment of the present invention.

Referring now to FIG. 20, therein is shown a top view of a coagulation measurement device 2000, in an embodiment of the present invention. The top view depicts a porous material 1702 surrounding a hydrophobic surface 2002 with a input filter 2004 that is pre-treated with a coagulation factor, having the input reservoir 1704 over it. The surface energy of the input filter is carefully controlled to both allow wicking of the fluid into it and electrohydrodynamic extraction of the filtered fluid. A first sensing electrode 2006 and a second sensing electrode 2008 are both covered by a thin coat of the dielectric layer 206. The first sensing electrode 2006 and the second sensing electrode 2008 are configured as parallel digits. The first co-planar electrode 302 and the second co-planar electrode 304 form the first parallel aligned pair 502, which borders a section of the hydrophilic porous material 1702 that extends from the input reservoir 102.

Whole blood is first introduced in the input reservoir 1704 and immediately permeates into the input filter 2004. The coagulation factor, within the input filter 2004, initiates clotting of the blood. The clotting causes displacement of the serum into the porous material 1702. The dielectric constant and the conductivity of the specimen in the filter, change as the blood coagulates. These changes result in a corresponding change in the impedance registered by the sensing electrodes underneath the input filter 2004. The sensing is done at high-enough frequency such that the variable capacitance and resistance between the electrodes dominate the measured response.

Figure 21:
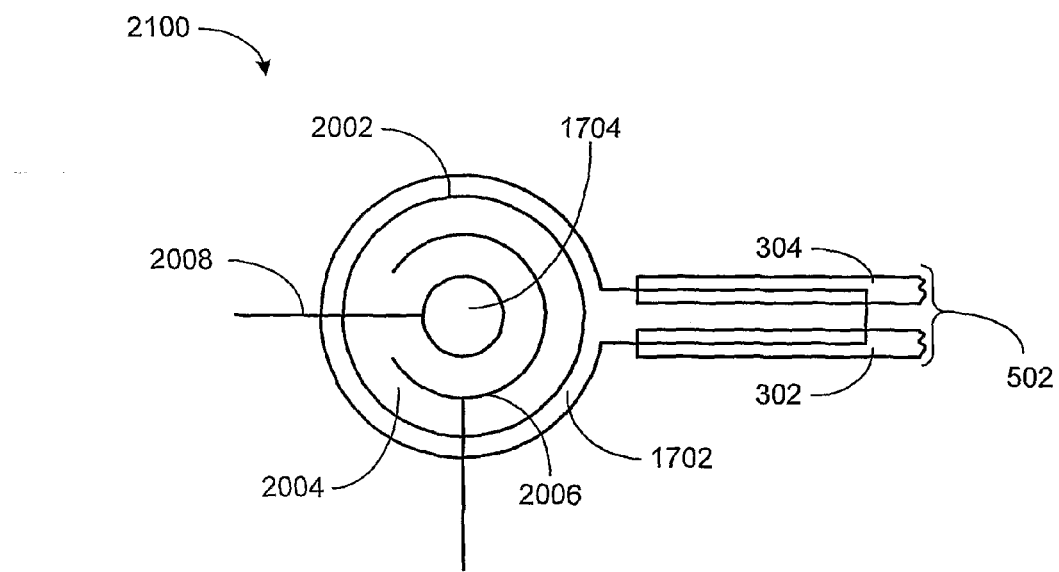
FIG. 21 is a top view of the coagulation measurement device, in an alternative embodiment of the present invention.

Referring now to FIG. 21, therein is shown a top view of the coagulation measurement device, in an alternative embodiment of the present invention. The block diagram depicts a porous material 1702 surrounding a hydrophobic surface 2002 with a input filter 2004 that is pre-treated with a coagulation factor, having the input reservoir 1704 over it. A first sensing electrode 2006 and a second sensing electrode 2008 are both covered by a thin coat of the dielectric layer 206. The first sensing electrode 2006 and a second sensing electrode 2008 are configured in a concentric circular pattern. The first co-planar electrode 302 and the second co-planar electrode 304 form the first parallel aligned pair 502, which borders a section of the porous material 1702 that extends from the input reservoir 102.

Figure 22:
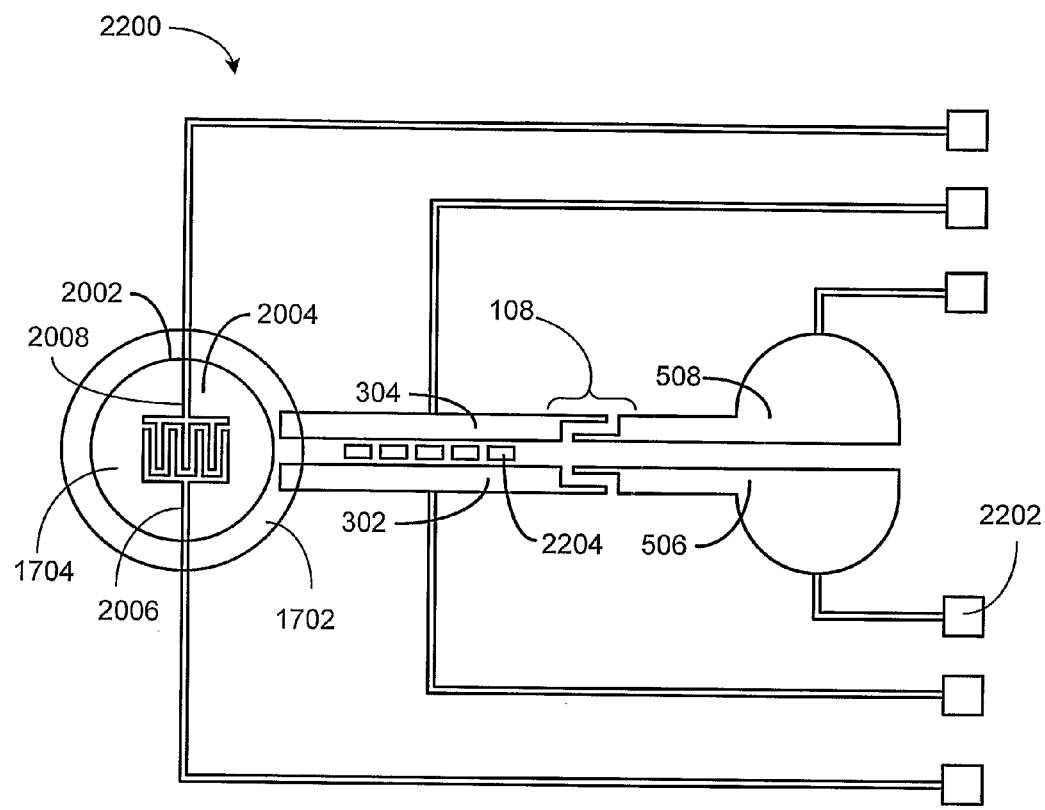
FIG. 22 is a top view of a microfluidic liquid stream configuration system, utilizing a single metal layer.

Referring now to FIG. 22, therein is shown a schematic diagram of a microfluidic liquid stream configuration system 2200, utilizing a single metal layer. The schematic-diagram, over the first sensing electrode 2006 and the second sensing electrode 2008, of the microfluidic liquid stream configuration system 2200 depicts a porous material 1702 surrounding a hydrophobic surface 2002 forming an input filter 2004 that is pre-treated with a coagulation factor, having the input reservoir 1704 over it. A first sensing electrode 2006 and a second sensing electrode 2008 are both covered by a thin coat of the dielectric layer 206. The first sensing electrode 2006 and the second sensing electrode 2008 are configured in an interlocking digit pattern of parallel digits. The first co-planar electrode 302 and the second co-planar electrode 304 border a section of the porous material 1702. As an alternative construction, the area around the hydrophobic surface 2002 may have a controlled surface chemistry, such as surface energy and functionality. The stop valve 108 is implemented on a single metal layer by offsetting a reduced width section. The third co-planar electrode 506 and the fourth co-planar electrode 508 form the continuation path from the stop valve 108. The interfaces for the electrodes are electrical contacts 2202. Assay chemistry areas 2204 are photolithographically defined between the first co-planar electrode 302 and the second co-planar electrode 304. The assay chemistry areas 2204 contain chemistries, such as fluorogenic substrates, immunochemestries, or affinity chemistries, for performing optical measurements. The measurements may include the detection of fluorescence, luminescence, chemiluminescence, or biochemiluminescence.

Figure 23:
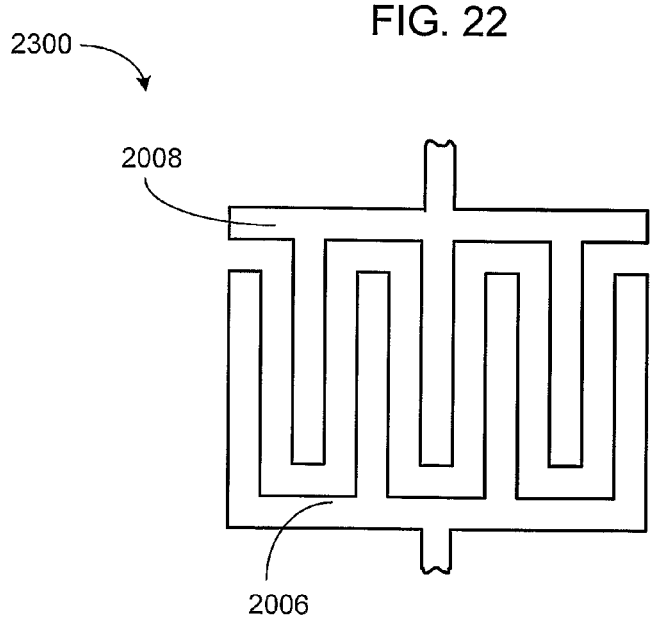
FIG. 23 is a close-up view of a coagulation monitor, of FIG. 22, in an alternative embodiment of the present invention.

Referring now to FIG. 23, therein is shown a close-up view of a coagulation monitor 2300, of FIG. 22, in an alternative embodiment of the present invention. The close-up view of the coagulation monitor 2300 depicts the first sensing electrode 2006 and the second sensing electrode 2008, which are configured in an interlocking digit pattern that contains parallel digits. The close proximity of the conductive traces allows an increased sensitivity to dielectric changes in the liquid over the coagulation monitor 2300. The coagulation monitor 2300 is covered by a thin dielectric film 206, which is coated by a coagulation factor. This element may be employed independently from the electrohydrodynamic elements or in combination with any flow delivery technology.

Figure 24:
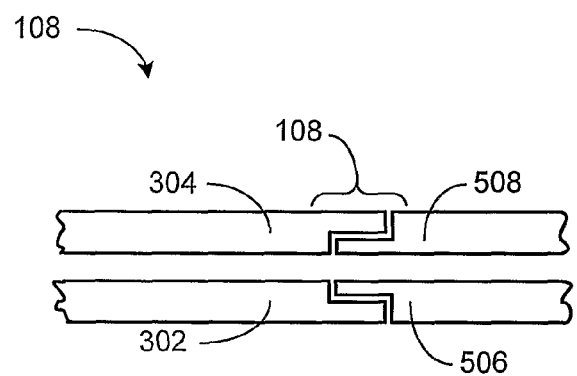
FIG. 24 is a close-up view of a single layer stop valve, of FIG. 22.

Referring now to FIG. 24, therein is shown a close-up view of a single layer stop valve 2400. The close-up view of the single layer stop valve 2400 depicts the first co-planar electrode 302 and the second co-planar electrode 304 having reduced width sections in the stop valve 108 area. The third co-planar electrode 506 and the fourth co-planar electrode 508 form the continuation path from the stop valve 108. They also have reduced width sections in the area of the stop valve 108. The reduced width sections are interlocked, but do not touch.

Figure 25:
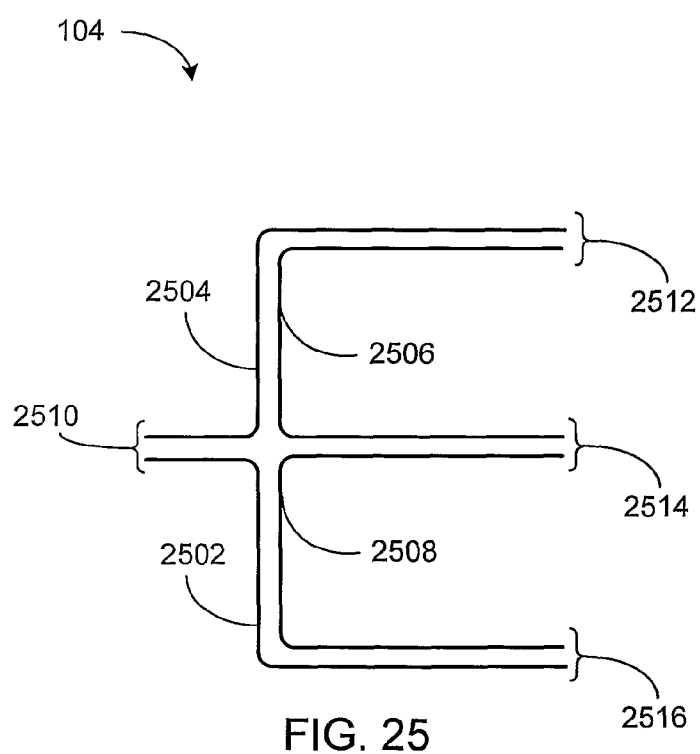
FIG. 25 is a schematic diagram of a multi-way selection valve, in an embodiment of the present invention.

Referring now to FIG. 25, therein is shown a schematic diagram of a multi-way selection valve 104, in an embodiment of the present invention. The schematic diagram of the multi-way selection valve 104 depicts a pattern formed by a first electrode 2502, a second electrode 2504, a third electrode 2506, and a fourth electrode 2508. The pattern defines an input 2510, a first output 2512, a second output 2514, and a third output 2516. In order for any electrode pair to move the liquid 208, of FIG. 2, one electrode must have a voltage and the adjacent electrode must be at a reference voltage, such as a ground. The sequence of voltage (V) and ground (G) that are used to activate the multi-way selection valve control is listed in Table 1. Activating the input 2510 comprises activating the combination of the first electrode 2502 and the second electrode 2504. Activating the first output 2512 comprises activating the input 2510 and activating the third electrode 2506.

TABLE 1

Activation Chart for Selected Outputs

| Electrode 2502 | Electrode 2504 | Electrode 2506 | Electrode 2508 | Output 2512 | Output 2514 | Output 2516 |
| --- | --- | --- | --- | --- | --- | --- |
| G | G | any | any | no flow | no flow | no flow |
| V | V | any | any | no flow | no flow | no flow |
| V | G | V | G | flow | flow | flow |
| V | G | G | G | no flow | no flow | flow |
| V | G | G | V | no flow | flow | no flow |
| V | G | V | V | flow | no flow | no flow |

Figure 26:
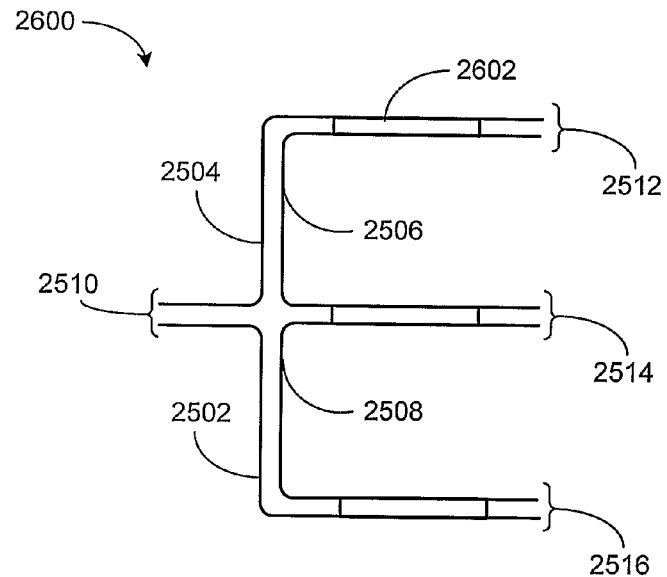
FIG. 26 is a schematic diagram of the multi-way selection valve having a porous additive region added to the output segments.

Referring now to FIG. 26, therein is shown a schematic diagram of the multi-way selection valve 2600 having a porous additive region 2602 added to the output segments. The schematic diagram of the multi-way selection valve 2600 depicts the multi-way selection valve of FIG. 25 with a porous additive region 2602 added to each of the output branches. The porous additive region 2602 of each branch may be pre-treated with a different antibody, enzyme substrate, coagulation factor, chemical functional groups, RNA, DNA, or other biological material or chemical entities. Having separate porous additive regions 2602 enables separate pre-treatment or measurement of each region without cross-contamination. In addition, the liquid may be incubated at delayed time intervals from a reference-time and for controlled lengths of time. As an alternative construction, the porous additive regions 2602 may be replaced by photolithographically defined regions containing specific surface chemistries used for measurements.

Figure 27:
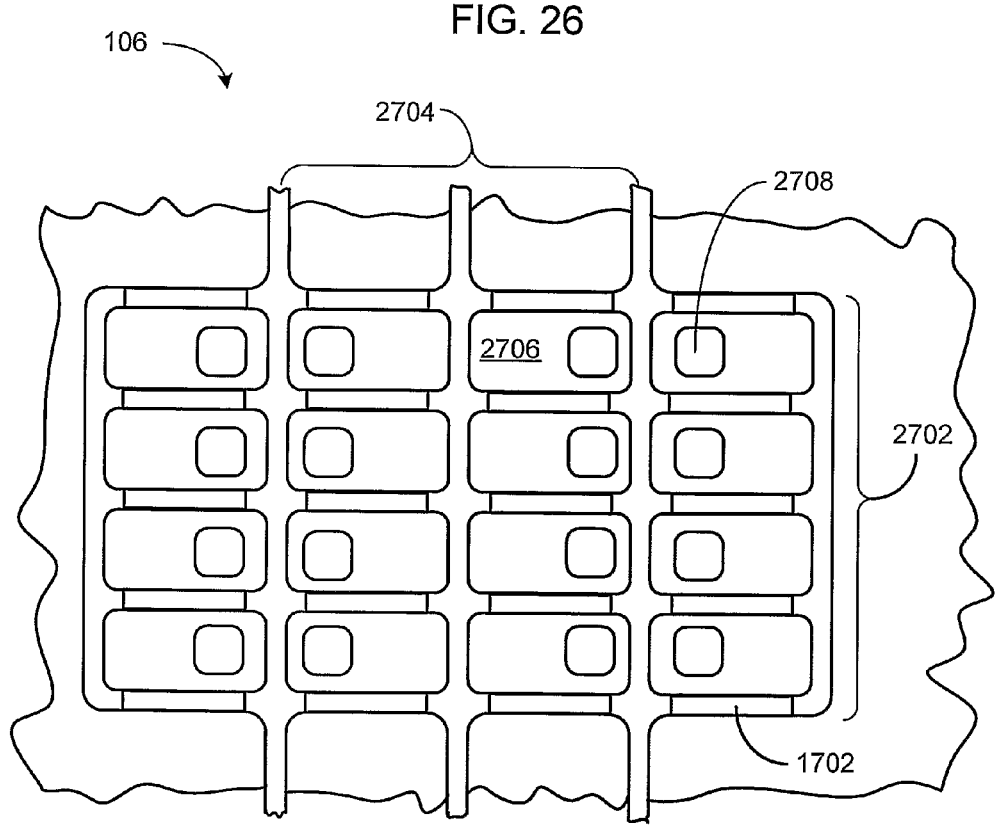
FIG. 27 is a top view of a generalized electro-hydrodynamic version of the analysis segment, in an embodiment of the present invention.

Referring now to FIG. 27, therein is shown a top view of a generalized electro-hydrodynamic version of the analysis segment 106, in an embodiment of the present invention. The top view of the analysis segment 106 depicts an analysis array 2702.

Electrode pairs 2704 may be arranged in one plane or multiple planes. The porous material 1702 may alternatively be a photolithographically defined surface region that may be pre-treated with biological or chemical entities to provide a means for (1) adding chemical components, such as reagents or biological substances, to the liquid 208, (2) performing immunoassays, (3) trapping certain chemical or biological components from the liquid 208, or (4) separating components of a liquid 208 sample. A closed electrode 2706 in the analysis segment 106 may have a central contact area 2708 that are accessed through the cover plate 602, of FIG. 6. This analysis segment is an example only and it is understood that the number of the closed electrode 2706 and co-planar electrode pairs 2704 may vary in number including forming an array of the closed electrodes 2706.

Figure 28:
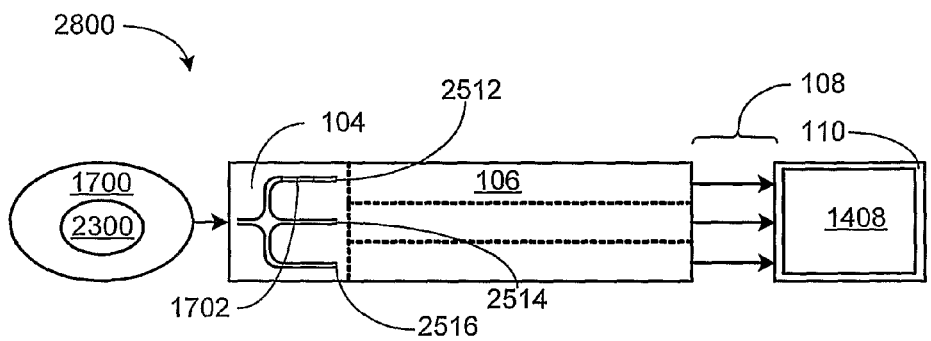
FIG. 28 is a block diagram of an enzyme activity system implemented by the microfluidic liquid stream configuration system.

Referring now to FIG. 28, therein is shown a block diagram of an enzyme activity system 2800 implemented by the microfluidic liquid stream configuration system 100. The block diagram depicts the electro-hydrodynamic liquid control element 1700 coupled to the multi-way selection valve 104. The first output 2512 of the multi-way selection valve 104 may have been mixed with a chemical agent that was deposited in the porous material 1702 prior to the analysis. The mixture of agents, dyes, or chemicals may be accomplished on the second output 2514 or the third output 2516 as well.

The stop valves 108 and the porous material 1702 may have optical sensors (not shown) collecting light or fluorescence associated with chemical or biochemical reactions, and the waste reservoir 110 may have hydrophilic material 1408 patterned in the waste capture region 1406. The first output 2512, of the multi-way selection valve 104, contains an enzyme substrate that emits fluorescence in the presence of an enzyme. The second output 2514, of the multi-way selection valve 104, contains the fluorescent product from the substrate. The third output 2516, of the multi-way selection valve 104, has no treatment. Fluorescence measurements may be performed over the porous regions with surface-linked reagents, which may be optically transparent. The first output 2512 of the multi-way selection valve 104 is the measurement channel, the second output 2514 is the positive control channel, and the third output 2516 is the negative control channel.

The electro-hydrodynamic liquid control element 1700 may also include the coagulation monitor 2300 in lieu of the input filter. The presence of the coagulation monitor 2300 enables the measurement of the Prothrombin Time (PT) and making the enzyme activity measurement from serum instead of plasma since as the blood clots, serum is transported to the rest of the system.

Figure 29:
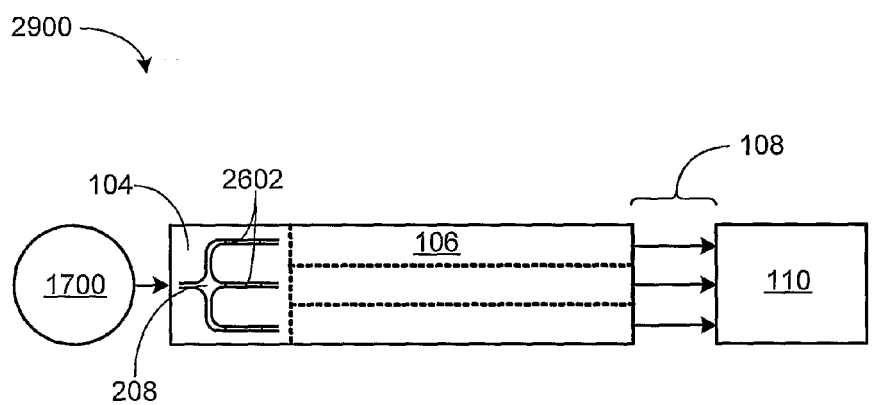
FIG. 29 is a block diagram of an immunoassay system implemented by the microfluidic liquid stream configuration system.

Referring now to FIG. 29, therein is shown a block diagram of an immunoassay system 2900 implemented by the microfluidic liquid stream configuration system. The block diagram depicts the electrohydrodynamic liquid control element 1700 that may be pre-treated with labeled reporter antibodies that are free to move with the liquid stream 210. The porous active region 2602 in the first two branches of the multi-way selection valve may contain immobilized capture antibodies specific to individual antigens. The porous active region 2602 in the third branch contains immobilized antibodies that bind to the reporter antibody. An optical readout is done at each of the porous active regions 2602 in the multi-way selection valve 104 and may monitor fluorescence, scattering, reflection, or absorption. The liquid 208 carries both the antigen and reporter antibody to the porous additive regions 2602 (i.e., the porous regions in the three way selection valve), where they form a sandwich assay with the capture antibodies. Unbound reporter antibodies are transported to the waste reservoir 110. The optical signal at the entrance of the waste reservoir 110 may be monitored to sense accumulation levels of the unbound reporter antibody.

Figure 30:
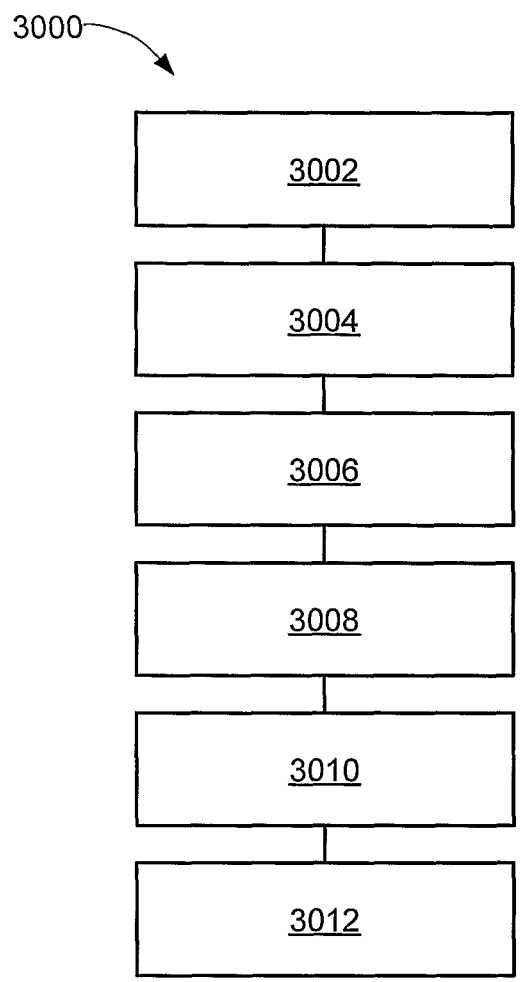
FIG. 30 is a flow chart of a microfluidic liquid stream configuration system for manufacturing the microfluidic liquid stream configuration system in an embodiment of the present invention.

Referring now to FIG. 30, therein is shown a flow chart of a microfluidic liquid stream configuration system 3000 for manufacturing the microfluidic liquid stream configuration in an embodiment of the present invention. The system 3000 includes providing a substrate in a block 3002; forming a first co-planar electrode and a second co-planar electrode on the substrate in a block 3004; applying a dielectric layer, with a controlled surface energy, on the first co-planar electrode and the second co-planar electrode in a block 3006; forming an input reservoir on the first co-planar electrode and a second co-planar electrode in a block 3008; supplying a liquid in the input reservoir for analysis in a block 3010; and imposing an electric field and an electric field gradient on the liquid for respectively driving surface charge and dipole moments in the liquid for configuring a liquid stream in a block 3012.

It has been discovered that the present invention thus has numerous aspects.

A principle aspect that has been unexpectedly discovered is that the present invention provides a flexible means for performing many types of chemical and biochemical analysis without moving parts or additional external equipment.

Another aspect is optical and electrical impedance measurements may be performed anywhere in the system as required for the application. The electrical measurements may be performed by superimposing an AC excitation to the driving voltage on the driving electrodes and measuring impedance changes. The optical measurements (absorbance, fluorescence, and chemiluminescence) are done through transparent top and bottom substrates.

Yet another important aspect of the present invention is that it valuably supports and services the historical trend of reducing costs, simplifying systems, and increasing performance.

These and other valuable aspects of the present invention consequently further the state of the technology to at least the next level.

Thus, it has been discovered that the microfluidic liquid stream configuration system of the present invention furnishes important and heretofore unknown and unavailable solutions, capabilities, and functional aspects for analysis of chemical and biochemical liquids. The resulting processes and configurations are straightforward, cost-effective, uncomplicated, highly versatile, accurate, sensitive, and effective, and can be implemented by adapting known components for ready, efficient, and economical manufacturing, application, and utilization.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hithertofore set forth herein or shown in the accompanying drawings are to be interpreted in an illustrative and non-limiting sense.

What is claimed is:

1. A method of manufacture of a microfluidic liquid stream configuration system comprising:
   providing a substrate;
   forming a first co-planar electrode coplanar with a second co-planar electrode on the substrate;
   applying a dielectric layer, with controlled surface energy, on the first co-planar electrode and the second co-planar electrode;
   forming a third electrode vertically overlapping the first co-planar electrode;
   forming a fourth electrode coplanar, aligned, and paired with the third electrode for accommodating various voltage levels for providing control and path of flow;
   forming an input reservoir over the first co-planar electrode and the second co-planar electrode for containing a liquid for analysis with an electric field, an electric field gradient, or a combination thereof across the first co-planar electrode and the second co-planar electrode, on the liquid for respectively driving surface charge or dipole moments in the liquid for configuring a liquid stream; and
   forming a multi-way selection valve coupled to the first co-planar electrode and the second co-planar electrode, the multi-way selection valve having an input and a first output, wherein the input is able to be activated by applying a voltage across the first co-planar electrode and the second co-planar electrode, and the first output is able to be activated by activating the input and applying a voltage to the third electrode.

2. The method as claimed in claim 1 further comprising:
   forming an analysis segment on the substrate comprising:
     forming an analysis array of a closed electrode in the analysis segment,
     patterning a porous material or a photolithographically defined surface region between the electrode pairs, and
     fabricating a cover plate having an opening over the analysis array, and
     wherein forming the analysis array includes forming the analysis array of the closed electrode connectable to a voltage through the opening in the cover plate, with the voltage variable across the electrode pairs for configuring a path through the analysis array and the liquid stream movable through the analysis array for adding chemical components, performing immunoassays, trapping components of the liquid stream, separating components of the liquid stream, or combination thereof.

3. The method as claimed in claim 1 further comprising:
   forming a waste reservoir on the substrate; and
   patterning a hydrophilic porous material in the waste reservoir; and
   wherein:
     forming the first co-planar electrode coplanar with the second co-planar electrode includes forming the first co-planar electrode and the second co-planar electrode for moving the liquid into the waste reservoir; and
     forming the input reservoir includes forming the input reservoir for collecting the liquid in the hydrophilic porous material.

4. A method of manufacture of a microfluidic liquid stream configuration system comprising:
   providing a substrate;
   forming a coagulation monitor, on the substrate, comprising:
      forming a first sensing electrode coplanar with a second sensing electrode on the substrate,
      applying a dielectric layer, with controlled surface energy, on the first sensing electrode and the second sensing electrode;
      forming a third electrode vertically overlapping the first co-planar electrode,
      forming a fourth electrode coplanar, aligned, and paired with the third electrode for accommodating various voltage levels for providing control and path of flow;
   patterning a porous material over the coagulation monitor;
   pre-treating the porous material with a coagulation factor;
   forming an input reservoir over the porous material for containing a liquid for analysis with an electric field, an electric field gradient, or a combination thereof across the first sensing electrode and the second sensing electrode, on the liquid for respectively driving surface charge or dipole moments in the liquid for configuring a liquid stream; and
   forming a multi-way selection valve coupled to the first co-planar electrode and the second co-planar electrode, the multi-way selection valve having an input and a first output, wherein the input is able to be activated by applying a voltage across the first co-planar electrode and the second co-planar electrode, and the first output is able to be activated by activating the input and applying a voltage to the third electrode; and
   wherein:
   forming the coagulation monitor includes forming the coagulation monitor for detecting changes in the impedance of the liquid in the input reservoir.

5. The method as claimed in claim 4 wherein forming the coagulation monitor includes forming the first sensing electrode and the second sensing electrode in a concentric circular shape.

6. The method as claimed in claim 4 wherein forming the coagulation monitor includes forming the first sensing electrode and the second sensing electrode as parallel digits.

7. A method of manufacture of a microfluidic liquid stream configuration system comprising:
   providing a substrate that is transparent or opaque;
   forming a first co-planar electrode coplanar with a second co-planar electrode on the substrate including the first co-planar electrode being parallel to the second co-planar electrode;
   applying a dielectric layer, with controlled surface energy, on the first co-planar electrode and the second co-planar electrode for isolating the first co-planar electrode from the second co-planar electrode;
   forming a third electrode vertically overlapping the first co-planar electrode;
   forming a fourth electrode coplanar, aligned, and paired with the third electrode for accommodating various voltage levels for providing control and path of flow;
   forming an input reservoir on the first co-planar electrode and the second co-planar electrode including forming an opening in a cover plate for containing a liquid for analysis in which the liquid is a chemical or biochemical compound and with the first co-planar electrode and the second co-planar electrode connectable to a voltage for imposing an electric field, an electric field gradient, or a combination thereof across the first co-planar electrode and the second co-planar electrode, on the liquid for respectively driving surface charge or dipole moments in the liquid for configuring a liquid stream; and forming a multi-way selection valve coupled to the first co-planar electrode and the second co-planar electrode, the multi-way selection valve having an input and a first output, wherein the input is coupled to the first co-planar electrode and the second co-planar electrode, the input is able to be activated by applying the voltage across the first co-planar electrode and the second co-planar electrode including applying the voltage and a ground, and the first output is able to be activated by activating the input and the third electrode.

8. The method as claimed in claim 7 further comprising:
   forming an analysis segment, on the substrate, comprising:
      forming an analysis array of a closed electrode in the analysis segment includes forming electrode pairs,
      patterning a porous material, a photolithographically defined surface region, or a combination thereof between the electrode pairs, and
      fabricating a cover plate having an opening over the analysis array, and
      wherein forming the analysis array includes forming the analysis array of the closed electrode connectable to the voltage through the opening in the cover plate and the voltage variable across the electrode pairs for configuring a path through the analysis array; and
   adding chemical components to the porous material or the photolithographically defined surface region; and
   wherein:
   forming the input reservoir includes forming the input reservoir for moving the liquid stream through the analysis array for adding the chemical components, performing immunoassays, trapping components of the liquid stream, separating components of the liquid stream, or a combination thereof.

9. The method as claimed in claim 7 further comprising:
   forming a waste reservoir on the substrate including forming the cover plate over the waste reservoir; and
   patterning a hydrophilic porous material in the waste reservoir including patterning the hydrophilic porous material between the substrate and the cover plate; and
   wherein:
   forming the first co-planar electrode coplanar with the second co-planar electrode includes forming the first co-planar electrode and the second co-planar electrode for moving the liquid into the waste reservoir; and
   patterning the hydrophilic porous material includes patterning the hydrophilic porous material for collecting the liquid in the hydrophilic porous material for enabling the continuous electrohydrodynamic actuation of the liquid.

10. A microfluidic liquid stream configuration system comprising:
   a substrate;
   electrical contacts on the substrate for applying a voltage;
   a first co-planar electrode on the substrate;
   a second co-planar electrode on the substrate and coplanar with the first co-planar electrode;
   a dielectric layer, having controlled surface energy, on the first co-planar electrode and the second co-planar electrode;
   an input reservoir formed over the first co-planar electrode and the second co-planar electrode for containing the liquid for analysis with an electric field, an electric field gradient, or a combination thereof across the first co-planar electrode and the second co-planar electrode, on the liquid for respectively driving surface charge or dipole moments in the liquid for configuring a liquid stream;
a third electrode vertically overlapping the first co-planar electrode; and
a fourth electrode coplanar, aligned, and paired with the third electrode for accommodating various voltage levels for providing control and path of flow; and
a multi-way selection valve coupled to the first co-planar electrode and the second co-planar electrode, the multi-way selection valve having an input and a first output, wherein the input is able to be activated by applying a voltage across the first co-planar electrode and the second co-planar electrode, and the first output is able to be activated by activating the input and applying a voltage to the third electrode.

11. The system as claimed in claim 10 further comprising an analysis segment on the substrate comprising:
an analysis array of closed electrodes having electrode pairs in the analysis segment;
a porous material or a photolithographically defined surface region between the electrode pairs; and
a cover plate having an opening over the closed electrodes for applying the voltage through the opening.

12. The system as claimed in claim 10 further comprising:
a waste reservoir on the substrate; and
a hydrophilic porous material in the waste reservoir for collecting the liquid; and
wherein:
the first co-planar electrode and the second co-planar electrode are for moving the liquid into the waste reservoir.

13. The system as claimed in claim 10 further comprising:
a cover plate having an opening for the input reservoir; and
a first aligned pair of electrodes in the input reservoir for moving the liquid stream.

14. The system as claimed in claim 13 wherein:
the multi-way selection valve coupled to the first co-planar electrode and the second co-planar electrode includes the input for activation by the voltage across the first co-planar electrode and the second co-planar electrode for application of the voltage and a ground, and the first output for activation by the input and for the voltage applied to the third electrode.

15. The system as claimed in claim 13 further comprising:
an analysis segment, on the substrate, includes a means for adding chemical components to the liquid;
closed electrodes in the analysis segment is part of an analysis array of electrodes pairs; and
a cover plate having an opening over the closed electrode includes an opening in the dielectric layer on the cover plate bottom for applying the voltage to the closed electrode through the opening.

16. The system as claimed in claim 13 further comprising:
a waste reservoir on the substrate having a cover plate over the waste reservoir; and
a hydrophilic porous material in the waste reservoir, between the substrate and the cover plate, for collecting the liquid; and
wherein:
the first co-planar electrode and the second co-planar electrode are for moving the liquid into the waste reservoir.

17. A microfluidic liquid stream configuration system comprising:
a substrate;
a coagulation monitor comprising:
a first sensing electrode on the substrate,
a second sensing electrode on the substrate and coplanar with the first sensing electrode, and
a dielectric layer, with controlled surface energy, on the first sensing electrode and the second sensing electrode;
an input reservoir over the coagulation monitor for containing a liquid for analysis with an electric field, an electric field gradient, or a combination thereof across the first sensing electrode and the second sensing electrode, on the liquid for respectively driving surface charge or dipole moments in the liquid for configuring a liquid stream;
a third electrode vertically overlapping the first co-planar electrode;
a fourth electrode coplanar, aligned, and paired with the third electrode for accommodating various voltage levels for providing control and path of flow;
a porous material coincident with the input reservoir;
a coagulation factor in the porous material;
a liquid in the input reservoir for analysis; and
a multi-way selection valve coupled to the first co-planar electrode and the second co-planar electrode, the multi-way selection valve having an input and a first output, wherein the input is able to be activated by applying a voltage across the first co-planar electrode and the second co-planar electrode, and the first output is able to be activated by activating the input and applying a voltage to the third electrode.

18. The system as claimed in claim 17 wherein the coagulation monitor includes the first sensing electrode and the second sensing electrode formed as parallel digits.

19. The system as claimed in claim 17 wherein the coagulation monitor includes the first sensing electrode and the second sensing electrode in a concentric circular shape.

\* \* \* \* \*